United States Patent
Yang

(10) Patent No.: US 6,596,735 B1
(45) Date of Patent: Jul. 22, 2003

(54) QUINOLINE DERIVATIVES USEFUL FOR INHIBITING FARNESYL PROTEIN TRANSFERASE

(75) Inventor: Bingwei V. Yang, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/724,464

(22) Filed: Nov. 28, 2000

Related U.S. Application Data

(60) Provisional application No. 60/170,119, filed on Dec. 10, 1999, and provisional application No. 60/168,207, filed on Nov. 30, 1999.

(51) Int. Cl.[7] .................. A61K 31/4709; C07D 215/38; C07D 401/06; C07D 403/10; A61P 35/00
(52) U.S. Cl. ................... 514/313; 514/314; 514/311; 546/159; 546/169; 546/173; 546/168; 546/170
(58) Field of Search .................. 546/159, 169, 546/173; 514/313, 314

(56) References Cited

U.S. PATENT DOCUMENTS

| 5,968,952 A | 10/1999 | Venet et al. ................. 514/312 |
| 6,037,350 A | * 3/2000 | Venet ......................... 514/312 |
| 6,258,824 B1 | * 7/2001 | Yang ......................... 514/312 |

FOREIGN PATENT DOCUMENTS

| WO | 9840383 | 9/1998 |
| WO | 9855124 | 12/1998 |
| WO | 0001386 | 1/2000 |

OTHER PUBLICATIONS

Khosravi–Far R et al. Cell Growth & Differentiation (1992). vol. 3, pp. 461–469.*
European Search Report for EP 1 106 612 A1.

* cited by examiner

Primary Examiner—Evelyn Mei Huang
(74) Attorney, Agent, or Firm—Peter C. Richardson; Paul H. Ginsburg; Krishna G. Banerjee

(57) ABSTRACT

The invention relates to compounds of the formula:

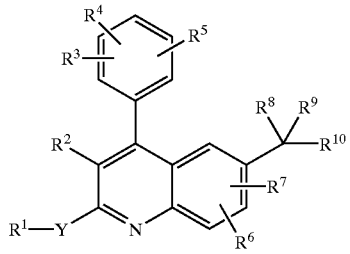

and to pharmaceutically acceptable salts and solvates thereof wherein Y, $R^1$, $R^2$, $R^3$, $R^4$, $R^5$, $R^6$, $R^7$, $R^8$, $R^9$, and $R^{10}$ have the meanings defined in the specification. The invention also relates to pharmaceutical compositions comprising said compounds and to the use of said compounds for inhibiting abnormal cell growth in mammals. The compounds of the above formula have activity as farnesyl protein transferase inhibitors.

15 Claims, No Drawings

QUINOLINE DERIVATIVES USEFUL FOR INHIBITING FARNESYL PROTEIN TRANSFERASE

This application claims the benefit of U.S. Provisional Application Nos. 60/170,119 and 60/168,207, filed Dec. 10, 1999 and Nov. 30, 1999, respectively.

BACKGROUND OF THE INVENTION

This invention relates to a series of quinoline derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as agents to combat tumors in which Ras contributes to transformation. Mutated, oncogenic forms of Ras are frequently found in many human cancers, most notably in more than 50% of colon and pancreatic carcinomas (Kohl et al., *Science, Vol.* 260, 1834 to 1837, 1993, incorporated herein in its entirety by reference). The compounds of the present invention exhibit activity as inhibitors of the enzyme farnesyl protein transferase and are therefore believed to be useful as anti-cancer and anti-tumor agents. Further, the compounds of the present invention may be active against any tumors that proliferate by virtue of farnesyl protein transferase.

Other compounds that are indicated as having activity inhibiting farnesyl protein transferase are referred to in International Publication Number WO 97/21701, entitled "Farnesyl Protein Transferase Inhibiting (Imidazol-5-yl) methyl-2-quinolinone Derivatives", which has an International Publication Date of Jun. 19, 1997; in International Publication Number WO 97/16443, entitled "Farnesyl Transferase Inhibiting 2-Quinolone Derivatives", which has an International Publication Date of May 9, 1997; U.S. Provisional Application No. 60/098,136, filed Aug. 27, 1998, entitled "Quinolin-2-one Derivatives Useful as Anticancer Agents"; U.S. Provisional Application No. 60/098,145, filed Aug. 27, 1998, entitled "Alkynyl-Substituted Quinolin-2-one Derivatives Useful as Anticancer Agents"; and U.S. Provisional Application No. 60/119,702, filed Feb. 11, 1999; all of which are incorporated herein by reference in their entireties.

SUMMARY OF THE INVENTION

The present invention relates to compounds of formula 1

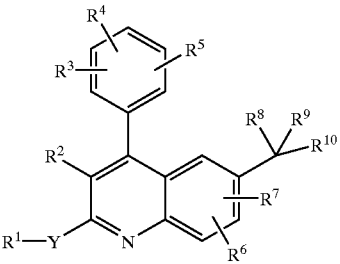

and to pharmaceutically acceptable salts and solvates thereof wherein:

Y is —$(CR^{13}R^{14})_n$— or —$NR^{13}$—, wherein n is zero, 1 or 2;

$R^1$ is H, —$(CR^{13}R^{14})$—O—$(C_1$–$C_6)$alkyl, $C_1$–$C_6$ alkyl, $C_2$–$C_6$ alkenyl, $C_2$–$C_6$ alkynyl, cyano, —$C(O)NR^{13}R^{14}$, —$C(O)R^{13}$, —$C(O)OR^{13}$, —$OC(O)R^{13}$, —$C(O)NR^{13}R^{14}$, $C_3$–$C_8$ cycloalkyl, phenyl, or —(4 to 6 membered heterocyclic); and wherein when Y is —$(CR^{13}R^{14})_n$— then $R^1$ can be further selected from —$NR^{13}R^{14}$, nitro, hydroxy, and azido; and wherein alkyl, cycloalkyl, phenyl, and heterocyclic moieties of the aforementioned $R^1$ substituents are optionally substituted with from one to three halogens;

$R^2$ is H, halo, cyano, $R^{11}$ or —$C(O)OR^{11}$, wherein cycloalkyl, aryl and heterocyclic moieties of said $R^2$ groups are optionally fused to a $C_6$–$C_{10}$ aryl group, a $C_5$–$C_8$ saturated cyclic group, or a 4 to 10 membered heterocyclic group, and wherein the foregoing $R^2$ groups, except H, halo, and cyano, but including any optional fused rings, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each $R^3$, $R^4$, $R^5$, $R^6$, and $R^7$ is independently selected from H, $R^{11}$, $C_2$–$C_{10}$ alkenyl, $C_2$–$C_{10}$alkynyl, halo, cyano, nitro, trifluoromethyl, trifluoromethoxy, azido, hydroxy, —$OR^{11}$, —$C(O)H$, —$C(O)OH$, —$C(O)R^{11}$, —$C(O)OR^{11}$, —$NR^{13}C(O)OR^{11}$, —$OC(O)H$, —$OC(O)R^{11}$, —$NR^{13}SO_2R^{11}$, —$SO_2NHR^{13}$, —$SO_2NR^{11}R^{13}$, —$NR^{13}C(O)H$, —$NR^{13}C(O)R^{11}$, —$C(O)NR^{13}H$, —$C(O)NR^{11}R^{13}$, —$NHR^{13}$, —$NR^{11}R^{13}$, —$CH=NOH$, —$CH=NOR^{11}$, —$S(O)_jH$, —$S(O)_jR^{11}$, wherein j is an integer from 0 to 2, —$(CR^{13}R^{14})_tC≡CH$, —$(CR^{13}R^{14})_tC≡CR^{11}$, —$(CR^{13}R^{14})_tC≡CSiH_2(R^{11})$, —$(CR^{13}R^{14})_tC≡CSiH(R^{11})_2$, and —$(CR^{13}R^{14})_tC≡CSi(R^{11})_3$; and wherein alkyl, alkenyl, cycloalkyl, aryl, and heterocyclic moieties of the foregoing $R^3$, $R^4$, $R^5$, $R^6$, and $R^7$ groups are optionally substituted by 1 to 3 substituents independently selected from halo, cyano, nitro, trifluoromethyl, trifluoromethoxy, azido, —$NR^{13}SO_2(C_1$–$C_6$ alkyl), —$SO_2NR^{13}R^{14}$, —$C(O)H$, —$C(O)(C_1$–$C_6$ alkyl), —$C(O)OH$, —$C(O)O(C_1$–$C_6$ alkyl), —$OC(O)H$, —$OC(O)(C_1$–$C_6$ alkyl), —$NR^{13}C(O)O(C_1$–$C_6$ alkyl), —$NR^{13}C(O)H$, —$NR^{13}C(O)(C_1$–$C_6$ alkyl), —$C(O)NR^{13}R^{14}$, —$NR^{13}R^{14}$, hydroxy, $C_1$–$C_6$ alkoxy, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), —$(CR^{13}R^{14})_t(C_3$–$C_{10}$ cycloalkyl), and —$(CR^{13}R^{14})_t($4 to 10 membered heterocyclic);

$R^8$ is H, cyano, hydroxy, $-(CR^{13}R^{14})_t$(4 to 10 membered heterocyclic), $-OR^{11}$, $-OC(O)H$, $-OC(O)R^{11}$, $-NR^{13}H$, $-NR^{11}R^{13}$, $-NR^{13}C(O)H$, $-C(O)OH$, $-C(O)OR^{11}$, $-SH$, or $-SR^{11}$, wherein heterocyclic groups of said $R^8$ groups are optionally substituted by 1 to 4 $R^6$ groups;

$R^9$ is $-(CR^{13}R^{14})_t$(imidazolyl) or $-(CR^{13}R^{14})_t$(pyridinyl), wherein said imidazolyl or pyridinyl moiety is optionally substituted by 1 or 2 $R^6$ substituents;

$R^{10}$ is phenyl or an aromatic 4 to 10 membered heterocyclic group, and said $R^{10}$ group is optionally substituted by 1 to 4 $R^6$ substituents;

each $R^{11}$ is independently $C_1-C_{10}$ alkyl, $-(CR^{13}R^{14})_t$($C_3-C_{10}$ cycloalkyl), $-(CR^{13}R^{14})_t$($C_6-C_{10}$ aryl), or $(CR^{13}R^{14})_t$(4 to 10 membered heterocyclic);

each $R^{13}$ and $R^{14}$ is independently H or $C_1-C_3$ alkyl;

and each t is an integer independently selected from 0 through 4.

In one embodiment, this invention provides compounds of formula 1, wherein $R^{10}$ is phenyl optionally substituted by 1 to 4 $R^6$ substituents.

In another embodiment, this invention provides compounds of formula 1 wherein Y is $-NR^{13}-$ or wherein n is zero.

In another embodiment, this invention provides compounds of formula 1 wherein $-Y-R^1$ is cyano or $-C(O)NR^{13}R^{14}$.

In another embodiment, this invention provides compounds of formula 1 wherein $-Y-R^1$ is $-C(O)NH_2$.

In another embodiment, this invention provides, compounds of formula 1 wherein $-Y-R^1$ is $-C(O)OR^{13}$.

In another embodiment, this invention provides, compounds of formula 1 wherein $-Y-R^1$ is $-NR^{13}R^{14}$.

In another embodiment, this invention provides compounds of formula 1 wherein $-Y-R^1$ is hydrogen.

In another embodiment, this invention provides compounds of formula 1 wherein $-Y-R^1$ is methyl.

In another embodiment, this invention provides compounds of formula 1, wherein $-Y-R^1$ is $-CH=CH_2$.

In another embodiment, this invention provides compounds of formula 1 wherein $R^8$ is hydrogen, methyl or $-CH=CH_2$.

In another embodiment, this invention provides compounds of formula 1 wherein $R^8$ is hydrogen, hydroxy, $-NR^{13}H$, or $-NR^{11}R^{13}$.

The structures of preferred compounds of the invention are set forth in the following Table 1:

TABLE 1

| Y—$R^1$ | $R^8$ |
|---|---|
| Me | OH |
| Me | $NH_2$ |
| Vinyl | OH |
| —CN | OH |

TABLE 1-continued

| Y—$R^1$ | $R^8$ |
|---|---|
| —CN | $NH_2$ |
| —$CONH_2$ | OH |
| —$CONH_2$ | $NH_2$ |
| —CONHMe | OH |
| —$CONMe_2$ | OH |
| $NH_2$ | OH |
| NHMe | OH |
| $NMe_2$ | OH |
| NHEt | OH |

In Table 1, "Et" represents an ethyl moiety, and "Me" represents a methyl moiety.

This invention also relates to a method of inhibiting abnormal cell growth in a mammal, including a human, comprising administering to said mammal an amount of a compound of the formula 1, as defined above, or a pharmaceutically acceptable salt or solvate thereof, that is effective in inhibiting farnesyl protein transferase. In the pharmaceutical compositions and methods of treatment described herein, "a compound of formula 1" includes not only formula 1 as set forth generically, but also each of the embodiments and preferred embodiments of the compounds of formula 1 described and claimed herein.

This invention also relates to a method of inhibiting abnormal cell growth in a mammal, including a human, comprising administering to said mammal an amount of a compound of the formula 1, as defined above, or a pharmaceutically acceptable salt or solvate thereof, that is effective in inhibiting abnormal cell growth.

The invention also relates to a method for the inhibition of abnormal cell growth in a mammal which comprises administering to said mammal a therapeutically effective amount of a compound of formula 1, or a pharmaceutically acceptable salt or solvate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a pharmaceutical composition for inhibiting abnormal cell growth in a mammal, including a human, comprising an amount of a compound of the formula 1, as defined above, or a pharmaceutically acceptable salt or solvate thereof, that is effective in inhibiting farnesyl protein transferase, and a pharmaceutically acceptable carrier.

This invention also relates to a pharmaceutical composition for inhibiting abnormal cell growth in a mammal, including a human, comprising an amount of a compound of the formula 1, as defined above, or a pharmaceutically acceptable salt or solvate thereof, that is effective in inhibiting abnormal cell growth, and a pharmaceutically acceptable carrier.

The invention also relates to a pharmaceutical composition for the inhibition of abnormal cell growth in a mammal which comprises a therapeutically effective amount of a compound of formula 1, or a pharmaceutically acceptable salt or solvate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens; and a pharmaceutically acceptable carrier.

"Abnormal cell growth", as used herein, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs. Examples of such benign proliferative diseases are psoriasis, benign prostatic hypertrophy and restenosis.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "cycloalkyl", as used herein, unless otherwise indicated, includes cyclic alkyl moieties wherein alkyl is as defined above. Multicyclic, such as bicyclic and tricyclic, groups are included in this definition.

The term "alkenyl", as used herein, unless otherwise indicated, includes alkyl moieties having at least one carbon-carbon double bond wherein alkyl is as defined above.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "heterocyclic", as used herein, unless otherwise indicated, means aromatic and non-aromatic heterocyclic groups (including saturated heterocyclic groups) containing one or more heteroatoms each selected from O, S and N, wherein each ring of a heterocyclic group has from 4 to 10 atoms. Non-aromatic heterocyclic groups may include rings having only 4 atoms, but aromatic heterocyclic rings must have at least 5 atoms. Heterocyclic groups of this invention unless otherwise indicated may contain one ring or more than one ring, i.e. they may be monocyclic or multicyclic, for example bicyclic (which may comprise non-aromatic and/or aromatic rings). Preferably, bicyclic heterocyclic groups of this invention contain 6–10 members in their ring systems. Monocyclic heterocyclic groups of this invention preferably contain 5 or 6 members. Aromatic multicyclic heterocyclic groups include benzo-fused ring systems. The heterocyclic groups of this invention can also include ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, piperidinyl, 1,2,3,6-tetrahydropyridinyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "pharmaceutically acceptable salt(s)", as used herein, unless otherwise indicated, includes salts of acidic or basic groups that may be present in the compounds of formula 1. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

Certain compounds of formula 1 may have asymmetric centers and therefore exist in different enantiomeric forms. All optical isomers and stereoisomers of the compounds of formula 1, and mixtures thereof, are considered to be within the scope of the invention. With respect to the compounds of formula 1, the invention includes the use of a racemate, one or more enantiomeric forms, one or more diastereomeric forms, or mixtures thereof. The compounds of formula 1 may also exist as tautomers. This invention relates to the use of all such tautomers and mixtures thereof.

The subject invention also includes prodrugs of compounds of formula 1, which prodrugs are derivatives of compounds of formula 1, which compounds comprise free amino groups, said derivatives comprising amide, carbamide, or peptide derivations of said amino groups. Such prodrugs can comprise an amino acid residue, or a polypeptide chain of two or more, such as up to four, amino acid residues, that are covalently joined through peptide bonds. Amino acid residues useful in preparing prodrugs of the invention include the 20 naturally-occurring amino acids designated by three letter symbols, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Preferred amino acid residues are those with a nonpolar group such as Ala, Val, Nval, Leu, Met, Gly, Pro, Phe, or a basic polar group such as Lys.

The subject invention also includes isotopically-labelled compounds, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples below, by substituting a readily available isotopically labelled reagent for a non-isotopically labelled reagent.

Patients that can be treated with compounds of formula 1, as defined above, or pharmaceutically acceptable salts or solvates thereof, according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The invention also relates to a pharmaceutical composition for the prevenuon of blastocyte implantation in a mammal which comprises a therapeutically effective amount of a compound of formula 1, or a pharmaceutically acceptable salt, prodrug or hydrate thereof, and a pharmaceutically acceptable carrier.

Patients that can be treated with compounds of formula 1, according to the methods of this invention also include patients suffering from abnormal cell growth, as defined above.

This invention also relates to a method of inhibiting abnormal cell growth in a mammal comprising administering to said mammal a therapeutically effective amount of a compound of formula 1, or a pharmaceutically acceptable salt or solvate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones and anti-androgens that is effective in inhibiting abnormal cell growth.

This invention also relates to a pharmaceutical composition for inhibiting abnormal cell growth in a mammal comprising an amount of a compound of formula 1, or a pharmaceutically acceptable salt or solvate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones and anti-androgens; and a pharmaceutically acceptable carrier.

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (celecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyi-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;

and pharmaceutically acceptable salts and solvates of said compounds.

Other anti-angiogenesis agents, including other COX-II inhibitors and other MMP inhibitors, can also be used in the present invention;

A compound of formula 1, can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application No. 60/113,647 (filed Dec. 23, 1998) which is incorporated by reference in its entirety, however other CTLA4 antibodies can be used in the present invention.

The compounds of formula 1 and their pharmaceutically acceptable salts, prodrugs and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

This invention also relates to a process for the preparation of a compound of formula 1, or a pharmaceutically acceptable salt or solvate thereof, comprising (a) hydrolysing a compound of formula 4, wherein R is $C_1$–$C_6$ alkyl, to yield a compound of formula 3 (b) treating the compound of formula 3 with a trifluoromethane sulfonyl containing reagent in the presence of a base, to yield the compound of formula 2 and (c) treating the compound of formula 2 with $R^1$—Y—L, wherein L is a B(OH)2, zinc, copper or tin derivative of $R^1$—Y, in the presence of (i) a triphenylphosphine or a bis(diphenylphosphino)alkyl compound and (ii) a palladium catalyst, with heating, thereby producing the compound of formula 1, wherein when $R^1$—Y—L is an amine, the conversion of compound of formula 2 to compound of formula 1 can be achieved by heating the mixture of a triflate and an amine neat or in a solvent such as THF or DMF at temperature of 70° to 110° C.

DETAILED DESCRIPTION OF THE INVENTION

In the following Schemes and Examples, "Et" represents an ethyl moiety, and "Me" represents a methyl moiety. Hence, for example, "OEt" means ethoxy. Also, "THF" means tetrahydrofuran, and "DMF" means dimethylformamide.

The compounds of formula 1 may be prepared as described below.

With reference to Scheme 1 below, the compounds of formula 1 may be prepared by reacting an intermediate triflate (trifluorosulfonate or "Tf"), with an intermediate of $R^1$—Y—L, wherein $R^1$ and Y are as defined above. L is selected from B(OH)$_2$, Zn, Cu, and Sn derivatives, in the presence of a triphenylphosphine or bis(diphenylphosphino) alkyl and a palladium catalyst, such as palladium acetate or Pd(PPh$_3$)$_4$, with or without a base such as sodium or potassium carbonate, and a solvent such as toluene, THF, DMF or dimethoxyethane at a temperature within the range of about 50–100° C. for a period of about 1 to 24 hours. When $R^1$—Y—L is an amine, the conversion of compound of formula 2 to compound of formula 1 can be achieved by heating the mixture of a triflate and an amine neat or in a solvent such as THF or DMF at temperature of 70° to 110° C.

Scheme 1

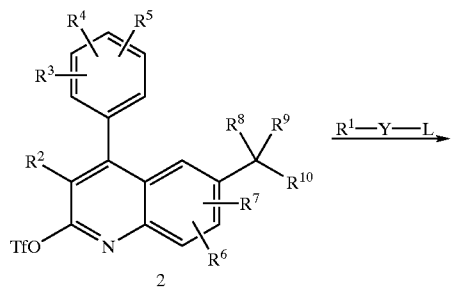

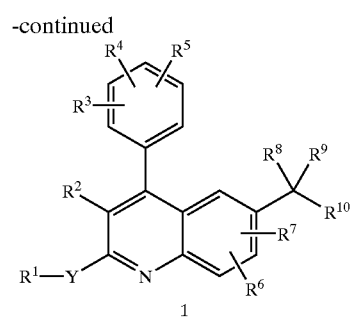

With reference to Scheme 2 below, the compounds of formula 2 can be prepared by reacting an intermediate of formula 3 with a trifluoromethane sulfonyl containing reagent, such as trifluoromethane sulfonic anhydride or PhHNTf, in the presence of a base, such as DMAP or 2,6-lutidine. The reaction initially involves the tautomerization of quinolone to 2-hydroxy-quinoline that is derivatized to the desired quinoline derivative.

Scheme 2

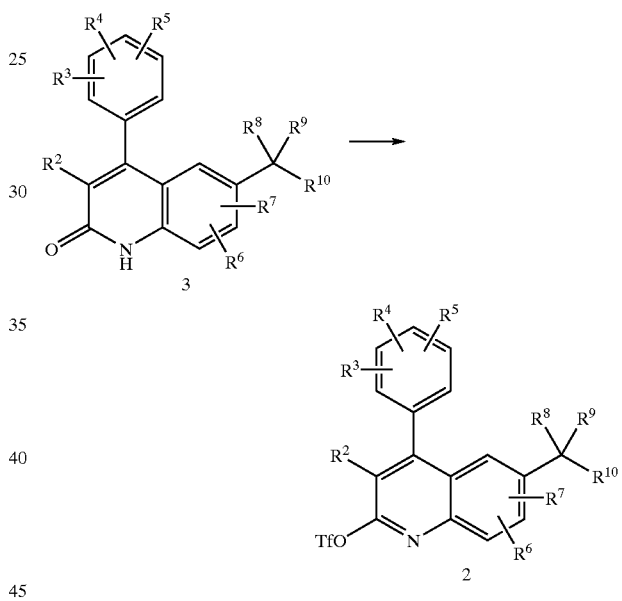

With reference to Scheme 3 below, the compounds of formula 3 may be prepared by hydrolysing an intermediate ether of formula 4, wherein R is $C_1$–$C_6$ alkyl, according to methods familiar to those skilled in the art, such as by stirring the intermediate of formula 4 in an aqueous acid solution, or in an organic solvent with a Lewis acid. An appropriate acid is, for example, hydrochloric acid. An appropriate Lewis acid and the solvent are, for example, iodotrimethylsilane and dichloromethane.

Scheme 3

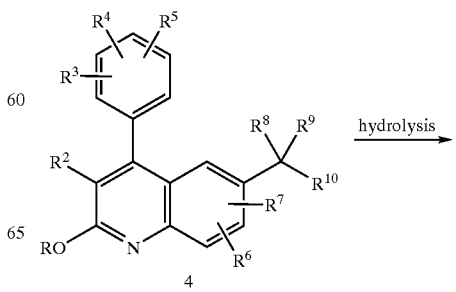

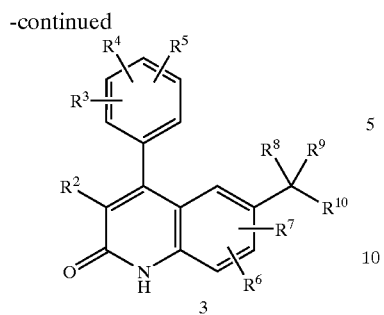

3

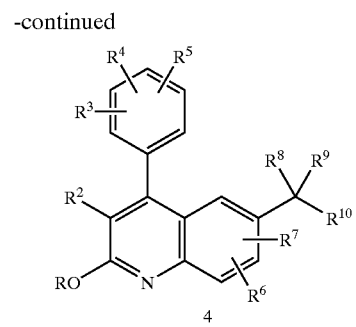

4

With reference to Scheme 4 below, the intermediate of formula 4, referred to above, may be prepared by reacting an intermediate of formula 5, wherein W is an appropriate leaving group, such as halo, with an intermediate ketone of formula 6. This reaction is done by converting the intermediate of formula 5 into an organometallic compound, by stirring it with a strong base such as butyl lithium, and subsequently adding the intermediate ketone of formula 6. Although at first instance, this reaction gives a hydroxy derivative ($R^8$ is hydroxy), said hydroxy derivative can be converted into other intermediates wherein $R^8$ has another definition by performing functional group transformations familiar to those skilled in the art.

Scheme 4

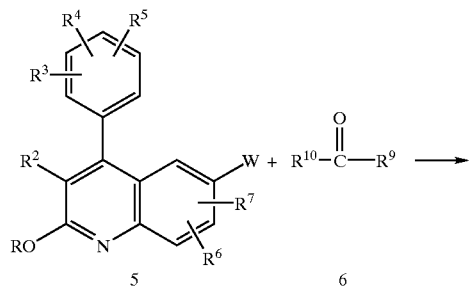

With reference to Scheme 5 below, compounds of formula 9 can be prepared by means of ring opening of the isoxazole moiety of the intermediate of formula 7 by stirring it with an acid, such as $TiCl_3$, in the presence of water. Subsequent treatment of the resulting intermediate of formula 8 with a suitable reagent, such as $R^2CH_2COCl$ or $R^2CH_2COOC_2H_5$, wherein $R^2$ is as defined above, yields either directly a compound of formula 9 or an intermediate which can be converted to a compound of formula 9 by treatment with a base, such as potassium tert-butoxide. The intermediate of formula 9 can be converted to an intermediate of formula 5 by stirring it with an 0-alkylation reagent, such as trimethyloxonium tetrafluoroborate ($BF_4OMe_3$) for a period of time, typically four to fifteen hours, and subsequently adding a strong base such as aqueous sodium hydroxide.

Scheme 5

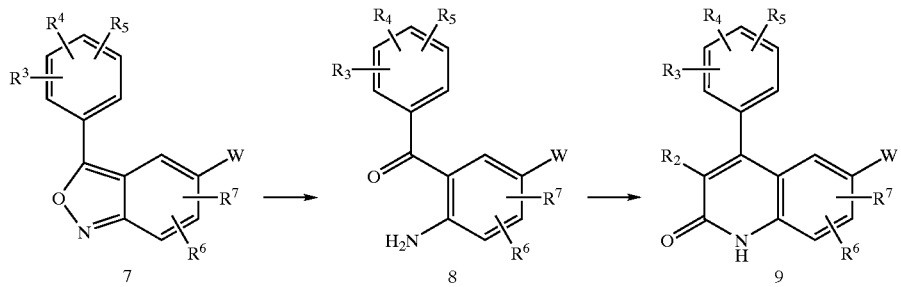

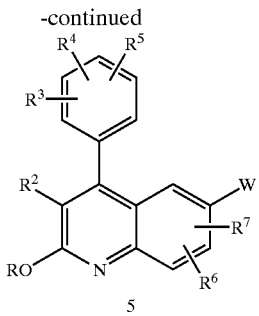

With reference to Scheme 6 below, compounds of formula 1d wherein $R^8$ is a radical of formula —$NR^{11}R^{13}$ wherein $R^{11}$ and $R^{13}$ are as described herein, may be prepared by reacting an intermediate of formula 11, wherein W is an appropriate leaving group, such as halo, with a reagent of formula 12. Said reaction may be performed by stirring the reactants in an appropriate solvent, such as tetrahydrofuran.

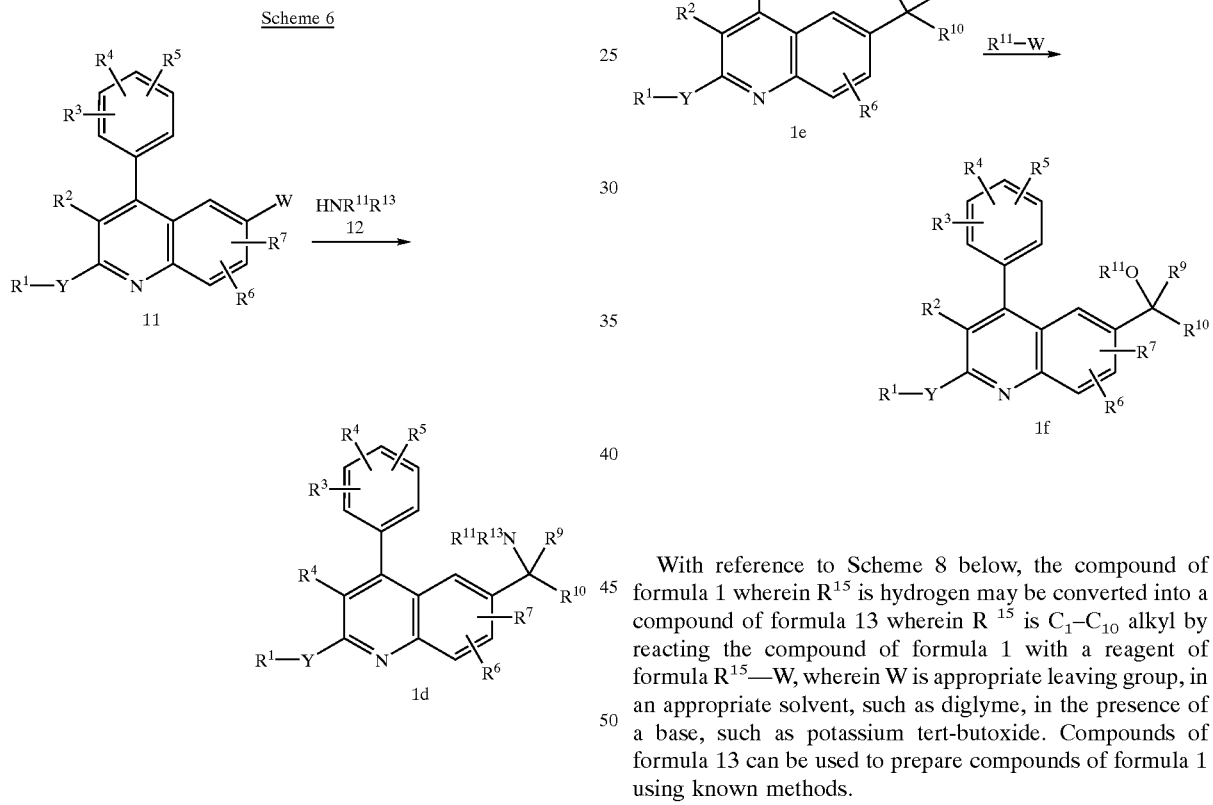

With reference to Scheme 7 below, compounds of formula 1 wherein $R^8$ is hydroxy (said compounds being represented by formula 1e) may be converted into compounds of formula 1f, wherein Rag has the meaning described herein except it is not hydrogen, or into compounds of formula 1 wherein $R^8$ is —OC(O)H or —OC(O)$R^{11}$, by methods known to those skilled in the art, including O-alkylation or O-acylation reactions; such as by reacting the compound of formula 1e with an alkylating reagent such as $R^{11}$—W, wherein $R^{11}$ is as described above, under appropriate conditions, such as in a dipolar aprotic solvent, such as DMF, in the presence of a base, such as sodium hydride. W is a suitable leaving group, such as a halo group or a sulfonyl group.

With reference to Scheme 8 below, the compound of formula 1 wherein $R^{15}$ is hydrogen may be converted into a compound of formula 13 wherein $R^{15}$ is $C_1$–$C_{10}$ alkyl by reacting the compound of formula 1 with a reagent of formula $R^{15}$—W, wherein W is appropriate leaving group, in an appropriate solvent, such as diglyme, in the presence of a base, such as potassium tert-butoxide. Compounds of formula 13 can be used to prepare compounds of formula 1 using known methods.

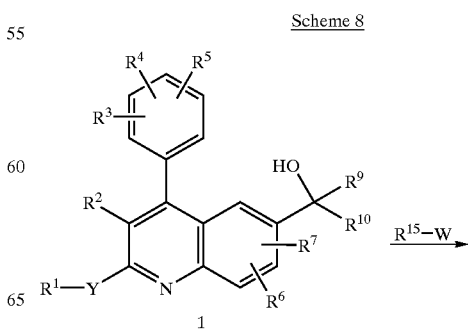

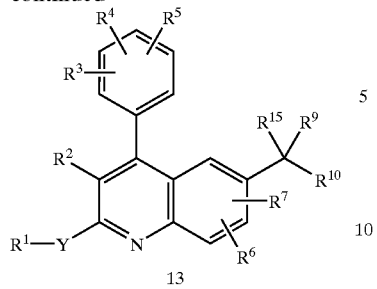

13

With reference to Scheme 9 below, compounds of formula 1h may be prepared by reacting a 2-cyanoquinoline of formula 1a with a peroxide such as hydrogen peroxide in an aprotic solvent such as DMSO, thus forming the corresponding amide on the 2-position of the quinoline of formula 1h wherein R' and R" are hydrogen. The compound of formula 1h wherein R' and R" are hydrogen may be transformed into a compound of formula 1h wherein R' and R" have a meaning as defined above apart from hydrogen by N-alkylation methods familiar to those skilled in the art.

Scheme 9

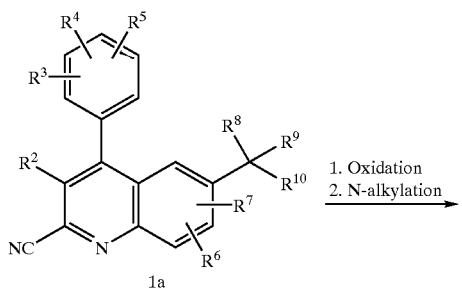

Alternatively, compounds of formula 1 can be prepared by reacting a nitrone of formula 6 with a sulfonyl containing electrophilic reagent, such as p-toluenesulfonylchloride, in the presence of a base, such as aqueous potassium carbonate. The reaction initially involves the formation of a 2-hydroxy-quinoline derivative which is subsequently tautomerized to the desired quinolinone derivative. The application of conditions of phase transfer catalysis, which are familiar to those skilled in the art, may enhance the rate of the reaction.

With reference to Scheme 10 below, intermediates of formula 15 may be prepared by reacting an intermediate of formula 14 with a trifluoromethane sulfonyl containing reagent, such as trifluoromethane sulfonic anhydride or PhHNTf, in the presence of a base, such as DMAP or 2,6-lutidine. The reaction initially involves the tautomerization of quinolone to 2-hydroxy-quinoline that is derivatized to the desired quinoline derivative.

Scheme 10

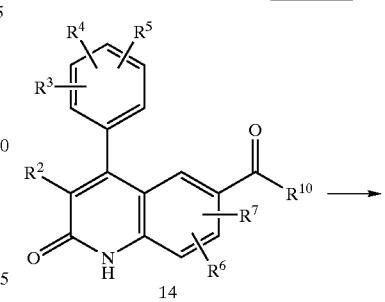

With reference to Scheme 11 below, the intermediate of formula 16 may be prepared by coupling an intermediate triflate (trifluoromethane sulfonate) of formula 15 with a compound of the formula $R^1$—Y—L, wherein $R^1$ is defined as above, and L is selected from $B(OH)_2$, Zn, Cu, and Sn derivatives, in the presence of a triphenylphosphine or bis(diphenylphosphino)alkyl and a palladium catalyst, such as palladium acetate or $Pd(PPh_3)_4$, with or without a base such as sodium or potassium carbonate, and a solvent such as toluene, THF, DMF or dimethoxyethane at the temperature within the range of about 50–100° C. for a period of about 1 to 24 hours. When $R^1$—Y—L is an amine, the conversion of compound of formula 15 to compound of formula 16 can be achieved by heating the mixture of a triflate and an amine neat or in a solvent such as THF or DMF at temperature of 70 to 100° C.

Scheme 11

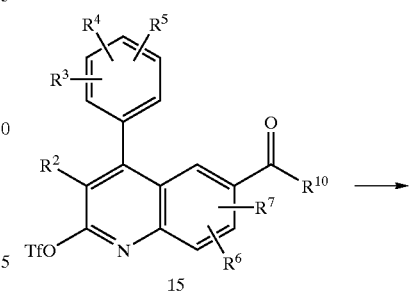

-continued

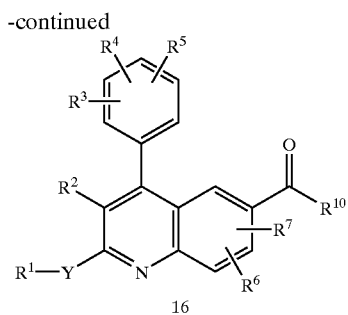

16

With reference to Scheme 12 below, the compound of formula 18 can be prepared by reacting a compound of formula 17 with an intermediate of formula 19 where $R^{24}$ is $SR^{23}$, and $R^{23}$ is hydrogen or phenyl. This reaction requires the presence of a suitable base, such as tert-butyl lithium (when $R^{23}$ is H) or lithium 2,2,6,6,-tetramethylpiperidine (when $R^{23}$ is phenyl), in an appropriate solvent, such as THF. The —$SR^{23}$ group can be reductively removed from the compound of formula 18 with RANEY™ nickel or oxidatively with nitric acid or aqueous hydrogen peroxide in acetic acid, resulting in a compound of formula 1. Alternatively, the compound of formula 18 can be prepared by reacting a compound of formula 17 with an intermediate of formula 19 wherein $R^{24}$ is $SiR^{25}R^{26}R^{27}$, and $R^{25}$, $R^{26}$, and $R^{27}$ are $C_1$–$C_6$ alkyl or phenyl. This reaction requires the presence of a suitable base, such as n-butyl lithium, in an appropriate solvent, such as THF. The $SiR^{25}R^{26}R^{27}$ group can be removed from the compound of formula 18 to obtain a compound of formula 1 by reaction with acetic acid or a fluoride reagent such as tetrabutylammonium fluoride (TBAF) in a solvent such as tetrahydrofuran.

Scheme 12

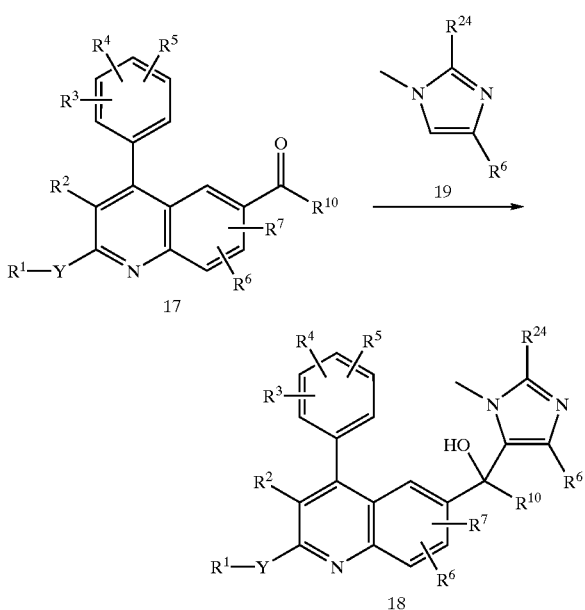

Compounds of formula 1 may also be prepared by an intramolecular photochemical rearrangement of compounds of formula 6, referred to above. Said rearrangement can be carried out by dissolving the reagents in a reaction-inert solvent and irradiating at a wavelength of 366 nm. It is advantageous to use degassed solutions and to conduct the reaction under an inert atmosphere, such as oxygen-free argon or nitrogen gas, in order to minimize undesired side reactions.

A substituent —Y—$R^1$ of a compound of formula 1 may be converted to another compound of formula 1 having a different —Y—$R^1$ substituent by means of reactions or functional group transformations familiar to those of ordinary skill in the art. A number of such transformations are already described above. Other examples are hydrolysis of amides to the corresponding carboxylic acids or amines; hydrolysis of nitriles to the corresponding amides; amino groups on imidazole or phenyl moieties may be replaced by hydrogen by diazotation reactions familiar to those skilled in the art, and subsequent replacement of the diazo-group by hydrogen; alcohols may be converted into esters and ethers; primary amines may be converted into secondary or tertiary amines; double bonds may be hydrogenated to the corresponding single bond.

The compounds of formula 1 and some of the intermediates described above may have one or more stereogenic centers in their structure. Such stereogenic centers may be present in a R or a S configuration.

The compounds of formula 1 as prepared in the above processes are generally racemic mixtures of enantiomers which can be separated from one another following resolution procedures familiar to those skilled in the art. The racemic compounds of formula 1 may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula 1 involves liquid chromatography using a chiral stationary phase. Said pure stereochemically isomeric forms may also be derived from the corresponding pure stereochemically isomeric forms of the appropriate starting materials, provided that the reaction occurs sterospecifically. Preferably if a specific stereoisomer is desired, said compound will be synthesized by stereospecfic methods of preparation. These methods will advantageously employ enantiomerically pure starting materials.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formula 1 are similarly prepared except through reaction of a carboxy group with an appropriate cationic salt reagent, such as sodium, potassium, calcium, magnesium, ammonium, N,N'-dibenzylethylenediamine, N-methylglucamine (meglumine), ethanolamine, tromethamine, or diethanolamine.

The compounds of formula 1 and their pharmaceutically acceptable salts and solvates (hereinafter referred to, collectively, as "the therapeutic compounds") can be administered orally, transdermally (e.g., through the use of a patch), parenterally, intravenously or topically. Oral administration is preferred. In general, compounds of the formula 1 and their pharmaceutically acceptable salts and solvates are most desirably administered in dosages ranging from about 1.0 mg up to about 500 mg per day, preferably from about 1 to about 100 mg per day in single or divided (i.e., multiple) doses. The therapeutic compounds will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The compounds of formula 1 exhibit activity as Ras farnesylation inhibitors and are useful in the treatment of cancer and the inhibition of abnormal cell growth in mammals, including humans. The activity of the compounds of formula 1 as Ras farnesylation inhibitors may be determined by their ability, relative to a control, to inhibit Ras farnesyl transferase in vitro. An example of one such procedure is described below.

A crude preparation of human farnesyl transferase (FTase) comprising the cytosolic fraction of homogenized brain tissue is used for screening compounds in a 96-well assay format. The cytosolic fraction is prepared by homogenizing approximately 40 grams fresh tissue in 100 ml of sucrose/$MgCl_2$/EDTA buffer (using a Dounce homogenizer; 10–15 strokes), centrifuging the homogenates at 1000×g for 10 minutes at 4° C., re-centrifuging the supernatant at 17,000 x g for 15 minutes at 4° C., and then collecting the resulting supernatant. This supernatant is diluted to contain a final concentration of 50 mM Tris HCl (pH 7.5), 5 mM DTT, 0.2 M KCl, 20 $\mu$M $ZnCl_2$, 1 mM PMSF and re-centrifuged at 178,000×g for 90 minutes at 4° C. The supernatant, termed "crude FTase" was assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 $\mu$L containing 50 mM N-(2-hydroxy ethyl) piperazine-N-(2-ethane sulfonic acid) (HEPES), pH 7.5, 30 mM $MgCl_2$, 20 mM KCl, 5 mM $Na_2HPO_4$, 5 mM dithiothreitol (DTT), 0.01% Triton X-100, 5% dimethyl sulfoxide (DMSO), 20 mg of crude FTase, 0.12 mM [$^3$H]-farnesyl pyrophosphate ([$^3$H]-FPP; 36000 dpm/pmole, Amersham LifeScience), and 0.2 $\mu$M of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 150 $\mu$L of steptavidin-coated SPA beads (TRKQ 7010) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, and inhibition of Bt-KTKCVIS interaction with FTase can be detected. The enzyme activity is saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-farnesyl in the presence of the test compound versus its incorporation in control wells (absence of inhibitor). $IC_{50}$ values, that is, the concentration required to produce half maximal farnesylation of Bt-KTKCVIS, is determined from the dose-responses obtained. In the assay described above, the compounds of the invention inhibited farnesyl transferase with characteristic $IC_{50}$ values in the subnanomolar to submicromolar range.

The following Examples 1–13 can be prepared according to the methods described above and are provided to illustrate aspects of the subject invention. They are not intended, nor should they be construed, to limit the invention as more fully described herein and set forth in the claims:

TABLE 1

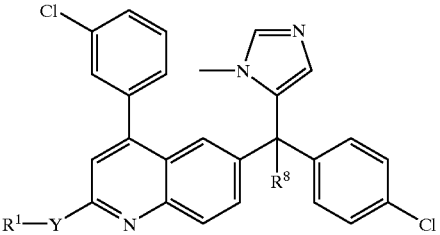

| Example | Y—$R^1$ | $R^8$ |
| --- | --- | --- |
| 1 | Me | OH |
| 2 | Me | $NH_2$ |
| 3 | Vinyl | OH |
| 4 | —CN | OH |
| 5 | —CN | $NH_2$ |
| 6 | —$CONH_2$ | OH |
| 7 | —$CONH_2$ | $NH_2$ |
| 8 | —CONHMe | OH |
| 9 | —$CONMe_2$ | OH |
| 10 | $NH_2$ | OH |
| 11 | NHMe | OH |
| 12 | $NMe_2$ | OH |
| 13 | NHEt | OH |

What is claimed is:

1. A compound of the formula:

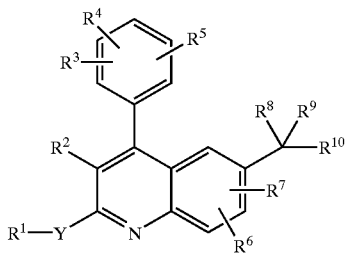

or a pharmaceutically acceptable salt or solvate thereof wherein:

Y is —$(CR^{13}R^{14})_n$— or —$NR^{13}$—, wherein n is 1 or 2;
$R^1$ is H, —$(CR^{13}R^{14})$—O—$(C_1–C6)$alkyl, $C_1–C_6$ alkyl, $C_2–C_6$ alkenyl, $C_2–C_6$ alkynyl, cyano, —C(O)$NR^{13}R^{14}$, —C(O)$R^{13}$, —C(O)$OR^{13}$, —OC(O)$R^{13}$, —C(O)$NR^{13}R^{14}$, $C_3–C_6$ cycloalkyl, phenyl, or —(4 to 6 membered heterocyclic); and wherein when Y is —$(CR^{13}R^{14})_n$— then $R^1$ can be further selected from —$NR^{13}R^{14}$, nitro, hydroxy, and azido; and wherein alkyl, cycloalkyl, phenyl, and heterocyclic moieties of the aforementioned $R^1$ substituents are optionally substituted with from one to three halogens;
$R^2$ is H, halo, cyano, $R^{11}$ or —C(O)$OR^{11}$, wherein cycloalkyl, aryl and heterocyclic moieties of said $R^2$ groups are optionally fused to a $C_6–C_{10}$ aryl group, a $C_5–C_8$ saturated cyclic group, or a 4 to 10 membered heterocyclic group, and wherein the foregoing $R^2$ groups, except H, halo, and cyano, but including any optional fused rings, are optionally substituted by 1 to 3 substituents independently selected from halo, cyano, nitro, trifluoromethyl, trifluoromethoxy, azido, —C(O)$R^{13}$, —C(O)$OR^{13}$, —OC(O)$R^{13}$, —$NR^{13}$C(O)$R^{14}$, —C(O)$NR^{13}R^{14}$, —$NR^{13}R^{14}$, hydroxy, $C_1–C_6$ alkyl, and $C_1–C_6$ alkoxy;
each $R^3$, $R^4$, $R^5$, $R^6$, and $R^7$ is independently selected from H, $R^{11}$, $C_2–C_{10}$ alkenyl, $C_2–C_{10}$alkynyl, halo, cyano, nitro, trifluoromethyl, trifluoromethoxy, azido, hydroxy, —$OR^{11}$, —C(O)H, —C(O)OH, —C(O)$R^{11}$, —C(O)$OR^{11}$, —$NR^{13}$C(O)$OR^{11}$, —OC(O)H, —OC(O)$R^{11}$, —$NR^{13}SO_2R^{11}$, —$SO_2NHR^{13}$, —$SO_2NR^{11}R^{13}$, —$NR^{13}$C(O)H, —$NR^{13}$C(O)$R^{11}$, —C(O)$NR^{13}$H, —C(O)$NR^{11}R^{13}$, —$NHR^{13}$, —$NR^{11}R^{13}$, —CH=NOH, —CH=$NOR^{11}$, —$S(O)_jH$, —$S(O)_jR^{11}$, wherein j is an integer from 0 to 2, —$(CR^{13}R^{14})_tC\equiv CH$, —$(CR^{13}R^{14})_tC\equiv CR^{11}$, —$(CR^{13}R^{14})_tC\equiv CSiH_2(R^{11})$, —$(CR^{13}R^{14})_tC\equiv CSiH(R^{11})_2$, and —$(CR^{13}R^{14})_tC\equiv CSi(R^{11})_3$; and wherein alkyl, alkenyl, cycloalkyl, aryl, and heterocyclic moieties of the foregoing $R^3$, $R^4$, $R^5$, $R^6$, and $R^7$ groups are optionally substituted by 1 to 3 substituents independently selected from halo, cyano, nitro, trifluoromethyl, trifluoromethoxy, azido, —$NR^{13}SO_2(C_1–C_6$ alkyl), —$SO_2NR^{13}R^{14}$, —C(O)H, —C(O)($C_1–C_6$ alkyl), —C(O)OH, —C(O)O($C_1–C_6$ alkyl), —OC(O)H, —OC(O)($C_1–C_6$ alkyl), —$NR^{13}$C(O)O($C_1–C_6$ alkyl), —$NR^{13}$C(O)H, —$NR^{13}$C(O)($C_1–C_6$ alkyl), —C(O)$NR^{13}R^{14}$, —$NR^{13}R^{14}$, hydroxy, $C_1–C_6$ alkoxy, $C_1–C_{10}$ alkyl, $C_2–C_{10}$ alkenyl, $C_2–C_{10}$ alkynyl, —$(CR^{13}R^{14})_t(C_6–C_{10})$, —$(CR^{13}R^{14})_t(C_3–C_{10}$ cycloalkyl), and —$(CR^{13}R^{14})_t(4$ to 10 membered heterocyclic);
$R^8$ is H, cyano, hydroxy, —$(CR^{13}R^{14})_t(4$ to 10 membered heterocyclic), —$OR^{11}$, —OC(O)H, —OC(O)$R^{11}$, —$NR^{13}H$, —$NR^{11}R^{13}$, —$NR^{13}$C(O)H, —C(O)OH, —C(O)$OR^{11}$, —SH, or —$SR^{11}$, wherein heterocyclic groups of said $R^8$ groups are optionally substituted by 1 to 4 $R^6$ groups;
$R^9$ is —$(CR^{13}R^{14})_t$(imidazolyl) or —$(CR^{13}R^{14})_t$(pyridinyl), wherein said imidazolyl or pyridinyl moiety is optionally substituted by 1 or 2 $R^6$ substituents;
$R^{10}$ is phenyl or an aromatic 4 to 10 membered heterocyclic group, and said $R^{10}$ group is optionally substituted by 1 to 4 $R^6$ substituents;
each $R^{11}$ is independently $C_1–C_{10}$ alkyl, —$(CR^{13}R^{14})_t(C_3–C_{10}$ cycloalkyl), —$(CR^{13}R^{14})_t(C_6–C_{10}$ aryl), or $(CR^{13}R^{14})_t(4$ to 10 membered heterocyclic);
each $R^{13}$ and $R^{14}$ is independently H or $C_1–C_3$ alkyl;
and each t is an integer independently selected from 0 through 4.

2. A compound according to claim 1, wherein $R^{10}$ is phenyl optionally substituted by 1 to 4 $R^6$ substituents.

3. A compound according to claim 1, wherein Y is —$NR^{13}$—.

4. A compound according to claim 1, wherein —Y—$R^1$ is methyl.

5. A compound according to claim 1, wherein $R^8$ is hydrogen, hydroxy, —$NR^{13}H$, or —$NR^{11}R^{13}$.

6. A method of inhibiting farnesyl protein transferase in a mammal comprising administering to said mammal an amount of a compound of claim 1, or a pharmaceutically acceptable salt or solvate thereof, that is effective in inhibiting farnesyl protein transferase.

7. A pharmaceutical composition for inhibiting farnesyl protein transferase in a mammal comprising an amount of a compound of claim 1 or a pharmaceutically acceptable salt or solvate thereof, that is effective in inhibiting farnesyl protein transferase, and a pharmaceutically acceptable carrier.

8. A compound of the formula:

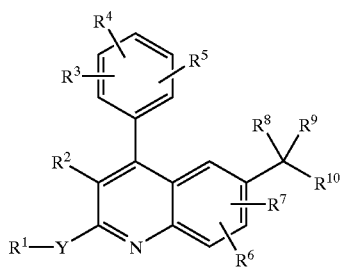

or a pharmaceutically acceptable salt or solvate thereof wherein:

Y is —$(CR^{13}R^{14})_n$— or —$NR^{13}$—, wherein n is zero;

$R^1$ is —$(CR^{13}R^{14})$—O—$(C_1$–$C_6)$alkyl, $C_1$–$C_6$ alkyl, $C_2$–$C_6$ alkenyl, $C_2$–$C_6$ alkynyl, cyano, —C(O)$NR^{13}R^{14}$, —C(O)$R^{13}$, —C(O)O$R^{13}$, —OC(O)$R^{13}$, —C(O)$NR^{13}R^{14}$, $C_3$–$C_6$ cycloaLkyl, phenyl, or —(4 to 6 membered heterocyclic); and wherein when Y is —$(CR^{13}R^{14})_n$— then $R^1$ can be further selected from —$NR^{13}R^{14}$, nitro, and azido; and wherein alkyl, cycloalkyl, phenyl, and heterocyclic moieties of the aforementioned $R^1$ substituents are optionally subsitruted with from one to three halogens;

$R^2$ is H, halo, cyano, $R^{11}$ or —C(O)O$R^{11}$, wherein cycloalkyl, aryl and heterocyclic moieties of said $R^2$ groups are optionally fused to a $C_6$–$C_{10}$ aryl group, a $C_5$–$C_8$ saturated cyclic group, or a 4 to 10 membered heterocyclic group, and wherein the foregoing $R^2$ groups, cxccpt H, halo, and cyano, but including any optional fused rings, are optionally substituted by 1 to 3 substituents independently selected from halo, cyano, nitro, trifluoromethyl, trifluoromethoxy, azido, —C(O)$R^{13}$, —C(O)O$R^{13}$, —OC(O)$R^{13}$, —$NR^{13}$C(O)$R^{14}$, —C(O)$NR^{13}R^{14}$, —$NR^{13}R^{14}$, hydroxy, $C_1$–$C_6$ alkyl, and $C_1$–$C_6$ alkoxy;

each $R^3$, $R^4$, $R^5$, $R^6$, and $R^7$ is indeptndently selected from $R^{11}$, $C_2$–$C_{10}$ alkenyl, $C_2$–$C_{10}$alkynyl, halo, cyano, nitro, trifluorornethyl, trifluoromethoxy, azido, hydroxy, —O$R^{11}$, —C(O)H, —C(O)OH, —C(O)$R^{11}$, —C(O)O$R^{11}$, —$NR^{13}$C(O)O$R^{11}$, —OC(O)H, —OC(O)$R^{11}$, —$NR^{13}SO_2R^{11}$, —$SO_2NHR^{13}$, —$SO_2NR^{11}R^{13}$, —$NR^{13}$C(O)H, —$NR^{13}$C(O)$R^{11}$, —C(O)$NR^{13}$H, —C(O)$NR^{11}R^{13}$, —$NHR^{13}$, —$NR^{11}R^{13}$, —CH=NOH, —CH=NO$R^{11}$, —S(O)$_j$H, —S(O)$_jR^{11}$, wherein j is an integer from 0 to 2, —$(CR^{13}R^{14})_t$C≡CH, —$(CR^{13}R^{14})_tC$=$CR^{11}$, —$(CR^{13}R^{14})_t$C≡CSiH$_2(R^{11})$, —$(CR^{13}R^{14})_t$C≡CSiH$(R^{11})_2$, and —$CR^{13}R^{14})_t$C≡CSi$(R^{11})_3$; and wherein alkyl, alkenyl, cycloalkyl, aryl, and heterocyclic moieties of the foregoing $R^3$, $R^4$, $R^5$, $R^6$, and $R^7$ groups are optionally substituted by 1 to 3 substituents independently selected from halo, cyano, nino, trifluoromethyl, trifluoromethioxy, azido, —$NR^{13}SO_2(C_1$–$C_6$ alkyl), —$SO_2NR^{13}R^{14}$, —C(O)H, —C(O)$(C_1$–$C_6$ alkyl —C(O)OH, —C(O)O$(C_1$–$C_6$ alkyl), —OC(O)H, —OC(O)$(C_1$–$C_6$ alkyl), —$NR^{13}$C(O)O$(C_1$–$C_6$ alkyl), —$NR^{13}$C(O)H, —$NR^{13}$C(O)$(C_1$–$C_6$ alkyl), —C(O)$NR^{13}R^{14}$, —$NR^{13}R^{14}$, hydroxy, $C_1$–$C_6$ alkoxy, $C_1$–$C_{10}$ alkyl, $C_2$–$C_{10}$ alkenyl, $C_2$–$C_{10}$ alkynyl, —$(CR^{13}R^{14})_t$$(C_6$–$C_{10}$ aryl), —$(CR^{13}R^{14})_t(C_3$–$C_{10}$ cycloalkyl), and —$(CR^{13}R^{14})_t$(4 to 10 membered heterocyclic);

$R^8$ is H, cyano, hydroxy, —$(CR^{13}R^{14})_t$(4 to 10 membered heterocyclic), —O$R^{11}$, —OC(O)H, —OC(O)$R^{11}$, —$NR^{13}$H, —$NR^{11}R^{13}$, —$NR^{13}$C(O)H, —C(O)OH, —C(O)O$R^{11}$, —SH, or —S$R^{11}$, wherein heterocyclic groups of said $R^8$ groups are optionally substituted by 1 to 4 $R^6$ groups;

$R^9$ is —$CR^{13}R^{14})_t$(imidazolyl) or —$(CR^{13}R^{14})_t$(pyridinyl), wherein said imnidazolyl or pyridinyl moiety is optionally substiruted by 1 or 2 $R^6$ substituents;

$R^{10}$ is phenyl or an aromatic 4 to 10 membered heterocyclic group, and said $R^{10}$ group is optionally substituted by 1 to 4 $R^6$ substituents, each $R^{11}$ is indteptndenlly $C_1$–$C_{10}$ alkyl, —$(CR^{13}R^{14})_t$$(C_3$–$C_{10}$ cycloalkyl), —$(CR^{13}R^{14})_t(C_6$–$C_{10}$ aryl), or $(CR^{13}R^{14})_t$(4 to 10 membered heterocyclic);

each $R^{13}$ and $R^{14}$ is indcpendently H or $C_1$–$C_3$ alkyl;

and each t is an integer independently selected from 0 through 4.

9. A compound according to claimr 8, wherein —Y—$R^1$ is cyano or —(O)$NR^{13}R^{14}$.

10. A compound according to claim 9, wherein —Y—$R^1$ is —C(O)$NH_2$.

11. A comnpound according to claim 8, wherein —Y—$R^1$ is —(O)O$R^{13}$.

12. A compound according to claim 8, wherein —Y—$R^1$ is —$NR^{13}R^{14}$.

13. A compound according to claim 8, wherein —Y—$R^1$ is CH=CH$_2$.

14. A method of inhibiting farnesyl protein transferase in a mammal comprising administering to said mammal an amount of a compound of claim 8, or a pharmaceutically acceptable salt or solvate thereof, that is effective in inhibiting famesyl protein transferase.

15. A pharmaceutical composition for inhibiting famesyl transferase in a mammal comprising an amount of a compound of claim 8, or a pharmaceutically acceptable salt or solvate thereof, that is effective in inhibiting famesyl protein transferase, and a pharmaceutically acceptable carrier.

* * * * *